United States Patent [19]

Nuzzio

[11] Patent Number: 5,578,178
[45] Date of Patent: Nov. 26, 1996

[54] MERCURY DROP ELECTRODE SYSTEM

[75] Inventor: Donald B. Nuzzio, Ringoes, N.J.

[73] Assignee: Analytical Instrument Systems, Inc., Ringoes, N.J.

[21] Appl. No.: 399,979

[22] Filed: Mar. 6, 1995

[51] Int. Cl.$^6$ ................................................. G01N 27/26
[52] U.S. Cl. ........................ 204/413; 43/73; 43/74
[58] Field of Search ..................... 204/413; 436/73, 436/74

[56] References Cited

U.S. PATENT DOCUMENTS

| | | | |
|---|---|---|---|
| 2,281,051 | 4/1942 | Roger | 221/148 |
| 2,361,295 | 10/1944 | Kanner et al. | 175/183 |
| 2,728,721 | 12/1955 | Ladisch | 204/413 |
| 2,745,803 | 5/1956 | Levegue | 204/413 |
| 2,849,391 | 8/1958 | Ladisch | 204/413 |
| 2,921,715 | 1/1960 | Asset et al. | 222/70 |
| 3,281,348 | 10/1966 | Schumacher et al. | 204/195 |
| 3,367,858 | 2/1968 | Kurosaki | 204/413 |
| 3,421,989 | 1/1969 | Haagen-Smit | 204/413 |
| 3,808,116 | 4/1974 | Webb | 204/413 |
| 4,260,467 | 4/1981 | Smith et al. | 204/195 |
| 4,846,955 | 7/1989 | Osteryoung et al. | 204/413 |
| 4,939,410 | 7/1990 | Nagy et al. | 204/413 |
| 5,294,324 | 3/1994 | Novotny | 204/413 |

FOREIGN PATENT DOCUMENTS

| | | |
|---|---|---|
| 515061 | 9/1976 | U.S.S.R. . |
| 674139 | 6/1952 | United Kingdom . |
| 936725 | 9/1963 | United Kingdom . |
| 936724 | 9/1963 | United Kingdom . |
| 1089600 | 11/1967 | United Kingdom . |

OTHER PUBLICATIONS

"A Renewable Mercury Microelectrode" by Novotny; Electroanalysis 2 (1990), p. 257.

"Automatic Mercury Drop Electrode With Double Solenoid Activated Valve" by Pedrotti, et al., Electroanalysis 4 (1992), pp. 635–642.

"Model 303 Static Mercury Drop Electrode–Operating and Service Manual" Princeton Applied Research, copyright 1979.

"Model K0020 Hanging Mercury Drop Electrode Kit–Operating and Service Manual" Princeton Applied Research, copyright 1978.

"Model 174/70 Drop Timer–Operating and Service Manual" Princeton Applied Research, copyright 1975.

"Adaptation of Poly(tetrafluoroethylene) Tips to Mercury Drop Electrodes and evaluation by Flow Injection Analysis", by Gutz, et al., Anal. Chem 1993, 65, pp. 500–503.

Catalog: Analogue Instruments for Polarography and Voltammetry by Metrohm.

*Primary Examiner*—Bruce F. Bell
*Attorney, Agent, or Firm*—Rohm & Monsanto

[57] ABSTRACT

A mercury drop arrangement tests electrochemically a sample solution, in a horizontal or vertical orientation, employing mercury which is delivered from a mercury reservoir to the test solution via a valve and mercury capillary tube. The mercury is valved to deliver one drop of mercury to the end of the capillary tube which is immersed in the sample solution. An electrochemical test of the sample solution can be performed when the mercury drop is in place, and if the mercury drop is not in place, the mercury in the capillary tube forms a microelectrode. The mercury capillary tube can easily be removed for replacement or cleaning when the valve is closed. Closing of the valve produces electrical isolation of the reservoir contents from the mercury in the mercury capillary tube, including the mercury drop itself. Such electrical isolation from the mercury reservoir precludes electrical noise generated in the reservoir from contaminating the voltammetric data. Environmental concerns are addressed by the invention in that mercury consumption is reduced, and operator exposure to mercury is eliminated. In addition, the invention facilitates remote control over the mercury electrode, and therefore is particularly adapted for monitoring harsh environments. Very small capillaries can be employed in the practice of the invention, and pressurization of the mercury reservoir facilitates initialization of the mercury electrode arrangement, and to prevent entrapment of air.

20 Claims, 5 Drawing Sheets

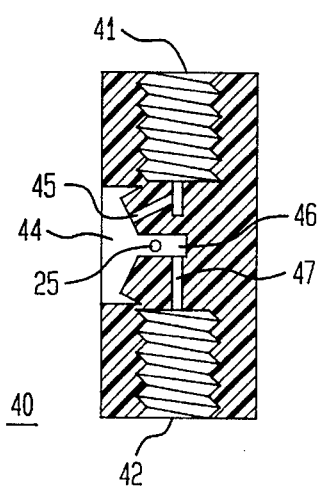
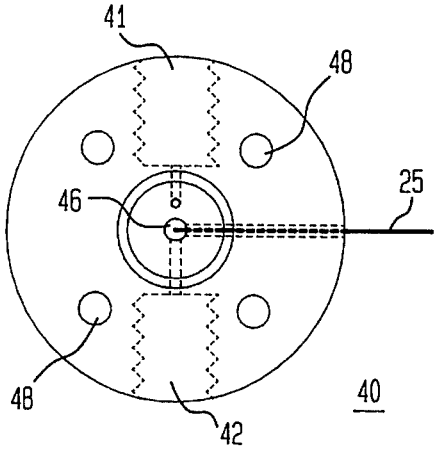
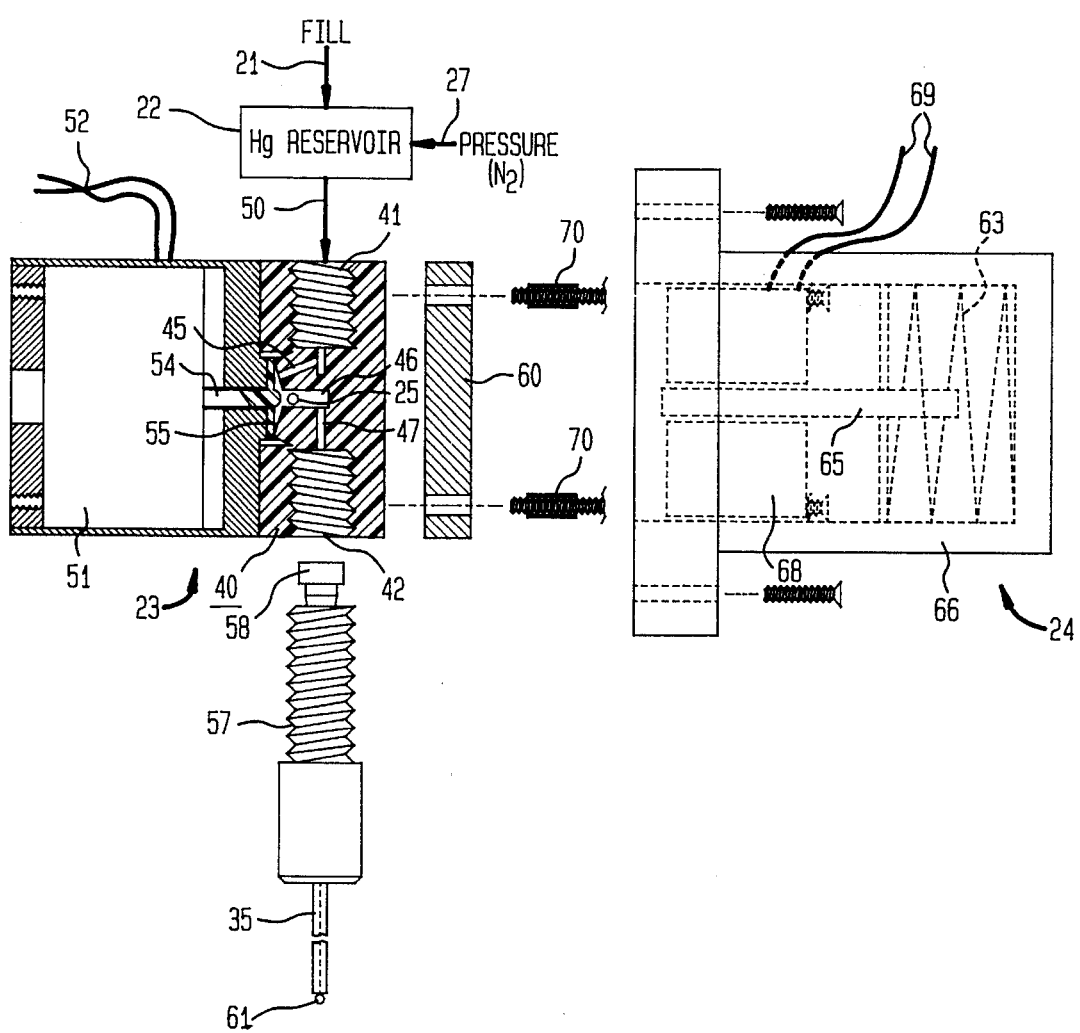

MERCURY DROP ELECTRODE SYSTEM

BACKGROUND OF THE INVENTION

1. Field of the Invention

This invention relates to a hanging mercury drop electrodes, and more particularly, to a mercury drop electrode that is controlled by valving and employs capillary tubes that produce mercury drops that hang at the end of a capillary during electrochemical testing procedures, such as the trace analysis of inorganic cations and anions.

2. Description of the Related Art

The use of a hanging mercury drop electrode for the analysis of ions has long been used by electrochemists in the study of trace heavy metals analysis. When a chemical species reacts to the mercury electrode it happens by means of the application of an electrical voltage to the working electrode, which may be formed of mercury. When a ionic species reacts to the voltage, the ionic species reduces, or oxidizes, on the surface of the mercury electrode. This reactions causes a current to flow. The current, which is proportional to the amount of chemical species ions in the solution under test, is measured. Once the electrochemical test is completed the mercury drop at the end of the capillary is removed and a fresh drop of mercury is deposited at the end of the capillary for the next analysis.

Electrodes of this type are particularly useful in the field of electrochemistry as renewable working electrodes, particularly in the field of polarography, which is a form of voltammetry at a mercury electrode, rather than at a solid electrode such as gold. When this mercury electrode system is placed in a test solution, various analytes in solution which exhibit the ability to oxidize or reduce (lose or gain ) electrons can be measured. Voltage is applied to the working electrode which in turns generates a current. The current is generated at the time of the oxidation or reduction of the analyte or analytes to be studied in the electrolyte solution, and is proportional to the amount of analyte or analytes present in the test solution.

Once the mercury drop is present at the end of the capillary which is dipped in the solution to analyze, the magnitude of the current associated with the above oxidation or reduction can be recorded. In a typical arrangement, a waveform voltage is applied between the working electrode and a reference electrode, while current is measured between the working electrode and the counter electrode immersed in the solution under test. The solution under test must have an adequate amount of supporting electrolyte present in order for electrical conduction in through the solution to occur. A non-aqueous solvent system can be used with this system but a organic soluble salt must be used to accomplish this electrical conduction through the solution.

The two types of voltammetry which utilize the mercury hanging drop electrode are the mentioned polarography, and stripping analysis. In polarography, any waveform, such as linear sweep, normal pulse, differential pulse, square wave pulse, etc. is applied to the working electrode surface. In stripping analysis, a plating or deposition time is added to the experiment to preconcentrate the analyte of interest on the mercury drop. A reverse waveform is then applied to strip off of the drop the plated analyte of interest. Not all elements have the properties necessary for performing strip analysis, but the technique is useful particularly with respect to heavy metals.

There is a need for a mercury drop electrode arrangement wherein the mercury drop remains intact during the performance of the selected electrochemical test. Conventional mercury drop electrode arrangements do not have facility for precise control over the size of the mercury drop itself. The mercury drops, therefore, are of inconsistent size and often are made too large whereby they shear or fall off of the electrode during the electrochemical test.

With respect to replacement of the mercury drop, the prior art has used several forms of dispensing and dislodging systems for mercury drops. These systems include, inter alia, the use of large bore capillaries and gravity feed techniques, which have been used over the years, and the use of a U-tube type which allows the mercury drop to be formed in a vertical mode on the end of the U tube. Another known arrangement utilizes a dispenser which is responsive to a solenoid system which controls the size of the mercury drop. The plunger which forms a seal and is immersed in the mercury in the reservoir. This known arrangement is very cumbersome and oftentimes results in mercury being sprayed in the laboratory environment during the installation of the mercury.

In some of the more modern polarographic techniques, the formation of the mercury drop must be correlated with the acquisition of voltammetric data from the sample solution. Such correlation usually requires the implementation of an extensive timing function for each new drop of mercury. There is a need for a mercury drop electrode arrangement which can perform a complete voltammetric study using only a single drop of mercury.

The dislodge solenoid in some known mercury drop electrode systems is located at a predetermined location along a capillary length. Misadjustment of this "striking type" of dislodge system frequently leads to the breaking of capillaries, requiring replacement of the capillaries on a regular basis. There is a need for a mercury drop dislodge arrangement which does not damage the capillaries. There is additionally a need for a mercury drop electrode system wherein the mercury drop can be dislodged from a remote location.

Another problem which is present in the prior art relates to the entrapment of air during the valving of mercury. This can result in a discontinuity of the electrical path between the mercury drop and the point to which the electronic measuring and monitoring equipment is coupled to receive the voltammetric data. In addition, the inclusion of air in the mercury path can result in contamination of the capillary, since the removal of a mercury drop will permit contraction of the air pocket, resulting in withdrawal of the mercury into the capillary and the introduction of the sample solution into the capillary tip. There is, therefore, a need in the art for an arrangement which avoids such entrapment of air.

A still further problem in the prior art results from the fact that the contact to the mercury drop at the end of the capillary is achieved via the mercury reservoir. In such a commonly used system, the mercury reservoir acts as an antenna which causes interference in the current measurements made at the mercury drop itself.

It is, therefore, an object of this invention to provide a mercury drop electrode arrangement wherein the consumption of mercury, which is expensive and toxic, is reduced.

It is another object of this invention to provide a mercury drop electrode arrangement wherein a relatively large reservoir of mercury is not in electrical communication with the mercury drop.

It is also an object of this invention to provide a mercury drop electrode arrangement wherein the size of the mercury drop can precisely be controlled.

It is a further object of this invention to provide a mercury drop electrode system which does not require the implementation of a timing function for correlating the acquisition of voltammetric data from the sample solution It is additionally an object of this invention to provide a mercury drop electrode system wherein an entire analysis of the solution under study is performed on that one drop.

It is yet a further object of this invention to provide a mercury drop electrode arrangement wherein the need to correlate multiple drops of mercury to voltammetric data for a given sample solution is not required.

It is also another object of this invention to provide a mercury drop electrode arrangement wherein the mercury drop can be dislodged from a remote location.

It is yet an additional object of this invention to provide a mercury drop electrode arrangement wherein the process of dislodgement of the mercury drop does not damage the capillary.

It is still another object of this invention to provide a mercury drop electrode arrangement wherein the likelihood of entrapment of air in the mercury reservoir is reduced.

It is a yet further object of this invention to provide a mercury drop electrode arrangement wherein electrical communication with the mercury drop does not include the mercury reservoir.

It is also a further object of this invention to provide a mercury drop electrode arrangement wherein interference effects caused by the mercury reservoir are eliminated.

It is additionally another object of this invention to provide a mercury drop electrode arrangement having an improved contact between the electrical connections of the mercury drop at the end of the capillary and a potentiostat which applies and measures the current.

A still further object of this invention is to provide a hanging mercury drop electrode arrangement which is easy to use and which achieves environmentally friendly goals, including reduction in the rate of consumption of mercury.

An additional object of this invention is to provide a mercury drop electrode arrangement which can be used with a variety of capillary materials, e.g., glass, Peek, Teflon®, fused silica, etc.

Yet another object of this invention is to provide a mercury drop electrode arrangement which can be operated remotely.

Another object of this invention is to provide a mercury drop electrode arrangement which can deliver mercury drops irrespective of whether the arrangement is in a horizontal or vertical orientation.

A yet further object of this invention is to provide a mercury drop electrode arrangement wherein the characteristics of a sample solution can be tested irrespective of whether a hanging drop of mercury is present on the end of the capillary tube.

It is also an additional object of this invention to provide a mercury drop electrode arrangement wherein the capillary tube can readily be removed for replacement or cleaning.

SUMMARY OF THE INVENTION

The foregoing and other objects are achieved by this invention which provides a mercury drop electrode arrangement having a reservoir for providing a source of liquid mercury. In accordance with a first apparatus aspect of the invention, a mercury capillary tube having an inlet, an outlet, and a mercury channel interconnecting the inlet and outlet, receives at the inlet liquid mercury from the reservoir and produces at the outlet a mercury drop. A dispense valve which is coupled at a reservoir thereof to the reservoir, and at a reservoir outlet thereof to the mercury capillary tube, controls the flow of the liquid mercury from the reservoir to the mercury capillary tube via a flow path therein. An actuator is additionally provided and is coupled to the dispense valve. The actuator has first and second states, whereby when the actuator is in the first state, the dispense valve is in a closed state the flow of the liquid mercury from the reservoir and the mercury capillary tube is discontinued and the liquid mercury in the reservoir is isolated electrically from the mercury drop at the outlet of the mercury capillary tube. When the actuator is in the second state, the dispense valve is in an open state and the flow of the liquid mercury from the reservoir and the mercury capillary tube is facilitated.

In one embodiment of the invention, the mercury drop electrode arrangement is further provided with a diaphragm which is disposed in the dispense valve and coupled to the actuator for controlling the flow path of the dispense valve and interrupting the flow of the liquid mercury from the reservoir and the mercury capillary tube when the actuator is in the first state. The diaphragm displaces a portion of the mercury in the flow path, whereby the mercury in the reservoir is isolated electrically from the mercury drop at the outlet of the mercury capillary tube. A contact region is provided in the flow path of the dispense valve, and a contact is provided therein, the contact having a mercury contact portion for communicating with the mercury in the contact region in the flow path of the dispense valve, and a terminal portion extending outward of the dispense valve for providing an electrical output signal responsive to the mercury in the contact region.

In a highly advantageous embodiment, the mercury capillary tube is formed of fused silica or PEEK.

Particularly when very small capillaries are employed, the reservoir can be pressurized slightly via a pressure port coupled to the reservoir for delivering a pressurized gas to the liquid mercury. In addition to facilitating initialization of the mercury electrode system, the pressurization greatly reduces the possibility of trapping air in the valve or in the mercury capillary tube.

The mercury drop of the electrode is removed by a mercury dislodge arrangement. In one embodiment, the mercury dislodge arrangement includes a dislodge solenoid which produces a mechanical shock upon being actuated electrically. A coupler transmits the mechanical shock from the dislodge solenoid to the dispense valve, and the resulting vibration causes the mercury drop to fall off of the tip of the mercury capillary tube.

The dislodge solenoid is provided with a plunger for moving in a predetermined direction upon applying an electrical actuation energy to the dislodge solenoid. An energy storage device, which may be a resilient spring, stores energy when the plunger is urged in the predetermined direction and releases the stored energy when the electrical actuation energy to the dislodge solenoid is discontinued.

In a further embodiment of the invention, the mercury dislodge arrangement utilizes a gas dispense valve having a gas inlet and a gas outlet for controlling the flow of a pressurized gas therebetween. A gas capillary having a gas capillary inlet is coupled to the gas outlet, and a gas capillary outlet thereof is arranged in the vicinity of the outlet of the mercury capillary tube. A pressurized gas flowing through the gas dispense valve and the gas capillary means dislodges and removes the mercury drop at the outlet of the mercury capillary tube.

In accordance with a further apparatus aspect of the invention, a mercury drop electrode arrangement is provided with a reservoir for providing a source of liquid mercury and a mercury capillary tube having an inlet, an outlet, and a mercury channel interconnecting the inlet and outlet, for receiving at the inlet liquid mercury from the reservoir and providing at the outlet a mercury drop. There is additionally provided a dispense valve coupled at a reservoir inlet thereof to the reservoir and at a reservoir outlet thereof to the mercury capillary tube for controlling a flow of the liquid mercury from the reservoir and the mercury capillary tube via a flow path therein. The dispense valve is additionally provided with a contact region interposed between the reservoir inlet and the reservoir outlet and a reservoir mercury path for channeling mercury from the reservoir inlet to the contact region. The reservoir mercury path has a reservoir mercury path outlet arranged distal from the reservoir inlet. There is additionally provided an outlet mercury path for channeling mercury from the contact region to the reservoir outlet, and a diaphragm for closing the reservoir mercury path outlet. An actuator is coupled to the diaphragm for urging the diaphragm selectably between closed and open positions with respect to the reservoir mercury path outlet.

The diaphragm is formed of electrically non-conductive material, and serves to isolate electrically the mercury in the reservoir from the mercury in the mercury capillary tube. An electrical contact is arranged to communicate electrically with the contact region of the dispense valve.

The reservoir, in a specific illustrative embodiment of the invention, is provided with a squeezable container for urging mercury through the dispense valve and the mercury capillary tube. This achieves the previously stated advantages of precluding the entrapment of air and personal contact with the mercury on the part of laboratory personnel.

In a further embodiment of this further aspect of the invention, the mercury drop electrode arrangement is further provided with a mercury drop dislodge arrangement which includes a dislodge solenoid for producing an electromagnetic force upon being actuated electrically, a plunger for moving in a predetermined direction in response to the electromagnetic force, an energy storage device for storing energy when the plunger is urged in the predetermined direction and releasing the stored energy when the electrical actuation energy to the dislodge solenoid is discontinued, and a backup plate coupler for coupling the dislodge solenoid to the dispense valve and transmitting a mechanical shock from the dislodge solenoid means to the dispense valve.

In a still further embodiment, the mercury dislodge arrangement includes a gas dispense valve having a gas inlet and a gas outlet for controlling the flow of a pressurized gas therebetween, a gas capillary having a gas capillary inlet coupled to the gas outlet, and a gas capillary outlet arranged in the vicinity of the outlet of the mercury capillary tube, whereby a pressurized gas flowing through the gas dispense valve and the gas capillary means will dislodge and remove the mercury drop at the outlet of the mercury capillary tube.

In accordance with a method aspect of the invention, a method of acquiring an electrical signal from a hanging drop of mercury includes the steps of:

urging mercury stored in a reservoir of mercury to flow through a valve in an open state and to flow through a mercury capillary tube to form the drop of mercury at a distal end of the mercury capillary tube;

closing the valve to discontinue the flow of mercury through the mercury capillary tube; and electrically isolating the mercury stored in the reservoir from the mercury in the mercury capillary tube.

In accordance with a specific illustrative embodiment of this method aspect of the invention, there is provided the additional step of communicating electrically with the drop of mercury, via the mercury in the mercury capillary tube, and via a contact extending through a wall of the valve.

Further in accordance with the method aspect of the invention, there are provided the further steps of:

dislodging the drop of mercury from the distal end of the mercury capillary tube;

opening the valve to resume the flow of mercury through the mercury capillary tube; and repeating the steps of urging mercury, closing the valve, and electrically isolating.

The hanging mercury drop electrode consists of a reservoir for holding the mercury, a valving system suitable to stop the flow of mercury, and a capillary tube through which the mercury is passed ultimately to form a drop of adequate size, on the order of several milligrams, at the end of the capillary tube. The inside diameter of the mercury capillary should be between 0.003" to 0.007" for the mercury droplet to form and stay on the end of the capillary tube which is immersed in a test solution. To achieve the objects stated, the hanging mercury drop electrode, is comprised of a mercury reservoir which can be the mercury container itself, which can be also pressurized if required with small bore capillaries, i.e., 0.003" or less in diameter. A dispense solenoid is actuated to allow the flow of mercury to the capillary tube.

The electrical contact system does not interfere with the electrical isolation of the contact from the mercury reservoir. Only the thread-like mercury in the mercury capillary tube and the mercury drop itself communicate electrically with the external potentiostat system.

The system of the present invention, in its various embodiments, can utilize either of two different types of dislodge solenoids. One solenoid can strike the dispense solenoid, the resulting vibrations in turn dislodging the mercury drop from the end of the capillary. In another embodiment, the system is operable in a remote mode wherein the dislodge solenoid is replaced with a pressurized gas valve which controls a stream of inert gas, i.e. , nitrogen, to be directed at the end of the capillary, thereby dislodging the mercury drop by operation of the force applied by the gas bubbles striking the mercury drop.

The present invention encompasses the following major components, the mercury capillary tube used to deliver drops of mercury to the test solution, the valve system which precisely delivers the mercury under manual or computer control, the contact to the mercury which isolates the capillary mercury from the reservoir above, and the mercury reservoir. The valve includes a diaphragm arrangement which is used to deliver or stop the flow of mercury from the system. The valve system of the present invention has incorporated therein a stainless steel contact which communicates electrically only the mercury within the valve and within the mercury capillary tube, not the mercury in the reservoir.

The capillary itself can be made from a variety of materials including plastic, glass, PEEK, and fused silica. The use of PEEK and the fused silica capillary, is new to the industry, and permits testing of a sample solution irrespective of whether the mercury capillary tube in a horizontal or a vertical orientation. As indicated, mercury is delivered from a mercury reservoir to the sample solution via an isolating dispense valve and the capillary tube. The mercury is valved so as to deliver one drop of mercury to the end of the mercury capillary tube which is immersed in the sample solution. An electrochemical test of that solution can be performed, in this inventive system, irrespective of whether the mercury drop is in place at the end of the mercury capillary tube. If the mercury drop is not in place, the mercury in the capillary tube forms a microelectrode. The capillary tube can easily be removed for replacement or cleaning during times when the valving device is not activated. Thus, the contents of the reservoir are maintained in electrical isolation, thereby eliminating electrical noise from the reservoir compartment from combining with the voltammetric data.

The system of the present invention has a beneficial environmental impact since significantly less overall mercury consumption is required in the daily operation of this device. The ability to control the mercury electrode remotely, as would be advantageous in monitoring harsh environments, is also a significant advantage of the inventive system. Environmental concerns are furthered by the invention's elimination of the need on the part of the operator or other laboratory personnel to handle the mercury during filling of the mercury reservoir, particularly when initiating a new hanging mercury drop system.

The mercury reservoir is adapted to employ a gravity feed for the mercury, or mercury delivery can be enhanced by the application of a slight pressure, illustratively of up to 5 psi, in order for the mercury to flow correctly through the valve system. Persons of skill in the art can, however, configure the system dimensions and pressures, as appropriate.

As previously stated, a significant problem with the known mercury drop electrodes is that air can readily become trapped in the reservoir and in the mercury capillary tube. The system of the present invention eliminates that problem by providing an arrangement whereby the operator squeezes the mercury reservoir container mounted above the dispense valve. This pressurized loading system greatly reduces the likelihood of entrapping air in the mercury reservoir, and allows the user to start the electrode system cleanly without the need to contact the mercury itself.

BRIEF DESCRIPTION OF THE DRAWING

Comprehension of the invention is facilitated by reading the following detailed description, in conjunction with the annexed drawing, in which:

FIG. 2 is a cross-sectional side view of a dispense valve body;

FIG. 3 is a partially phantom end view of the dispense valve body of FIG. 1;

FIG. 4 is a partially cross-sectional exploded illustration of a dispense valve and a dislodge valve assembly;

DETAILED DESCRIPTION

Figure 1:
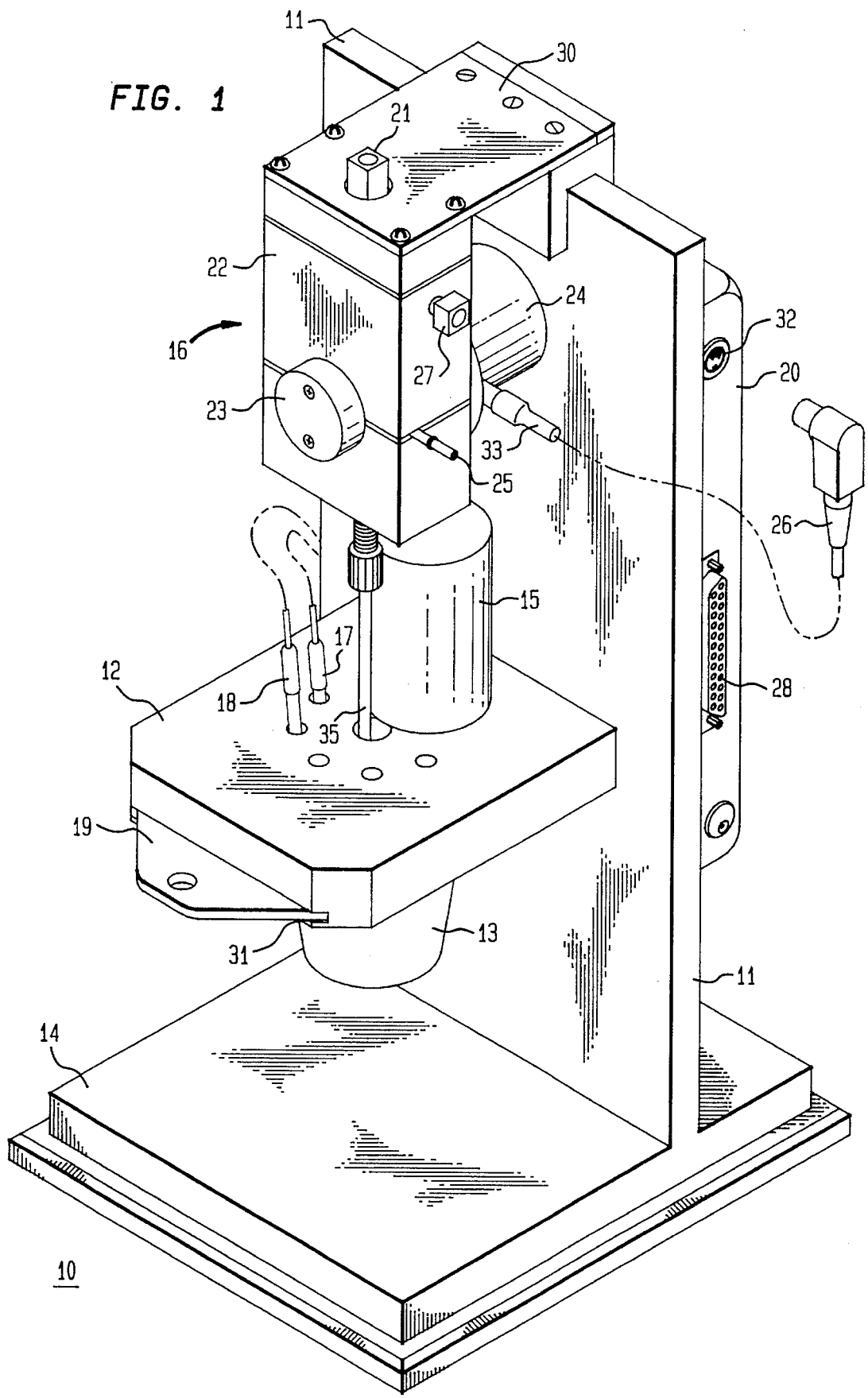
FIG. 1 is an isometric representation of an electrochemical cell on a stand, including a mercury electrode constructed in accordance with the principles of the invention.

FIG. 1 is an isometric representation of a mercury electrode system 10, constructed in accordance with the principles of the invention. As shown in this figure, mercury electrode system 10 includes a support stand 11. The support stand has a support base 14 at its lowermost extent. As shown, a support block 12 is coupled to the support stand, the support block being arranged to support an electrochemical cell 13. A stirrer 15 is shown to be mounted on support block 12, and stirs the sample solution (not shown in this figure).

A mercury electrode assembly 16 is coupled to a bracket arrangement 30 which is shown to be engaged at the top support stand 11. A counter electrode 17 and a reference electrode 18 are shown as passing through respective apertures in the support block, so as to communicate with the sample solution (not shown in this figure).

An electrochemical cell removal/securing tab 19 engages with slots 31 in the support block for facilitating removal and installation of electrochemical cell 13 with respect to the support block. In this specific illustrative embodiment of the invention, electrochemical cell 13 is engaged with electrochemical cell removal/securing tab 19. Of course, any other arrangement for coupling the electrochemical cell to the support block can be employed by persons of skill in the art in the practice of the invention.

Supporting electronics (not shown) for controlling the operation of mercury electrode system 10 are contained within an electronics module 20 which is installed on the reverse side of support stand 11. The supporting electronics, in this specific illustrative embodiment of the invention, are employed to control the operation of a dispense solenoid 23 and a dislodge solenoid 24. The dispense and dislodge solenoids are coupled to electronics module 20 via a control cable 26, which is shown to be interconnectable between an input terminal 33 of the solenoids and an input 32 of the electronics module. Input 32 of the electronics module is shown in this specific illustrative embodiment of the invention to be a 5-pin DIN socket. The control of mercury electrode system 10 can be effected by computer (not shown), by coupling the computer to a computer communications port 28.

Mercury (not shown) is loaded into mercury reservoir 22 through a mercury loading port 21. The mercury reservoir is, as shown, disposed directly beneath the mercury loading port. As discussed herein, mercury from mercury reservoir 22 is caused to flow through a mercury capillary tube 35, which is shown to extend through support block 12 and into the sample solution (not shown in this figure) in electrochemical cell 13. In the practice of the invention, mercury capillary tube 35 may be formed of glass, PEEK, Teflon®, fused silica, etc. Electrical contact with the mercury in the mercury capillary tube is achieved at a mercury contact 25.

In embodiments of the invention where the capillaries being used are extremely small, it may be desirable to utilize pressure from an external source (not shown) to enhance the flow of mercury therethrough. Such an optional pressurization feature would employ a pressurization port 27.

FIG. 2 is a cross-sectional side view of a dispense valve 40. This figure illustrates the flow path of the mercury (not shown) from the reservoir (not shown in this figure) which would be coupled at reservoir inlet 41 to the head of the mercury capillary tube (not shown in this figure), which would be coupled, as will be described herein, to outlet 42. In this specific illustrative embodiment of the invention, reservoir inlet 41 is in the form of a ¼-28 female thread. A diaphragm valve region 44 accommodates a diaphragm valve element (not shown in this figure) which will be described below with respect to FIG. 4. However, FIG. 2 shows a reservoir path 45 which allows the mercury to flow from the reservoir inlet to the diaphragm valve region 44. During times when the diaphragm (not shown in this figure) is in the open state, the mercury will flow from diaphragm valve region 44, through a contact region 46 and down an outlet path 47 to outlet 42.

Mercury contact 25 is arranged to be in electrical communication with the mercury (not shown) located in contact region 46, and consequently in electrical communication with the mercury path which extends to the tip of mercury capillary tube 35 (not shown in this figure), which, as will be described below, is coupled to dispense valve 40 at outlet 42 and extends into the sample solution (not shown in this figure). Also as will be discussed hereinbelow, at such times as the diaphragm valve element (not shown in this figure) is in the closed state, reservoir path 45 will be closed off and isolated electrically from contact region 46. Thus, mercury contact 25 will not be in electrical communication with the mercury in the reservoir. In the practice of the invention, the body of dispense valve 40 can be made from a variety of materials including, without limitation, stainless steel, poly ethetherketone (PEEK), Teflon®, Kel-F®, etc. Persons of skill in the art can select an appropriate material, without undue experimentation. However, a non-metallic material provides the advantage of not contaminating the mercury with another metal. A totally inert valve body is important in electrochemical studies which seek to determine trace levels of metals.

FIG. 3 is a partially phantom end view of dispense valve 40 shown in FIG. 2. This figure shows mercury contact 25 to extend from contact region 46 to the exterior of the dispense valve. As stated, this arrangement advantageously produces electrical contact only to the mercury in the capillary, and not the mercury in the reservoir. The mercury contact can be made from a variety of materials including, for example, stainless steel or other electrically conductive materials or metals which do not dissolve (amalgamate) with mercury.

Dispense valve 40 is configured to have a generally round shape, which conforms dimensionally to the dispense and dislodge solenoids, described hereinabove with respect to FIG. 1. Apertures 48 are used for the passage of assembly screws (not shown in this figure) for securing the dispense valve to the solenoids.

FIG. 4 is a partially cross-sectional and partially phantom exploded illustration of dispense valve 40, dispense solenoid 23, and dislodge solenoid 24. In addition, this figure shows, in schematic form, mercury reservoir 22 with mercury loading port 21 and pressurization port 27. The schematic illustration further shows arrow 50 which represents that mercury from mercury reservoir 22 is caused to flow to reservoir inlet 41. Mercury reservoir 22 can be a prefabricated unit, or in some embodiments of the invention, a standard one-pound type bottle of mercury. The present invention eliminates the need for personal contact by the operator with the mercury.

Dispense solenoid 23 is shown in FIG. 4 to have a dispense solenoid coil 51 to which electrical activation energy is provided via input leads 52. Upon actuation of the dispense solenoid, a plunger 54 is urged in the left-hand direction, bringing with it the central portion of diaphragm 55. The diaphragm, in this figure, is shown in the valve-open state, with the diaphragm in the left-most position. In this position, mercury is permitted to flow through reservoir path 45, through contact region 46, and through output path 47 to mercury capillary tube 35. However, when dispense solenoid coil 51 is deactivated, plunger 54 returns toward the right, as does diaphragm 55, closing off reservoir path 45. Not only is flow from the reservoir path discontinued, but the mercury is removed by the diaphragm from the region between the reservoir path and the contact region, and thereby the mercury in the reservoir path (as well as the mercury in the reservoir) is made electrically isolated from contact region 46. In a preferred embodiment of the invention, plunger 54 and diaphragm 55 are formed of inert materials which do not contaminate the mercury, such as Teflon® or Kel-F®. In the system of the present invention, therefore, the mercury in the reservoir is not included in the electrical circuit from which the voltammetric data is obtained at contact 25.

Mercury capillary tube 35 is shown to be engaged with a securing nut 57 having a sealing ferrule 58 therein. The securing nut threadedly engages with the internal threads of outlet 42 of the dispense valve.

In this specific illustrative embodiment of the invention, a backup plate 60 is interposed between the dispense valve and dislodge solenoid 24. The backup plate, which may be formed of stainless steel, is used by the dislodge solenoid to vibrate mercury drop 61 loose from the end of mercury capillary tube 35.

In dislodge solenoid 24, actuation of a solenoid coil 68 via electrical leads 69 causes an impact plunger 65 to be urged toward the fight, compressing a spring 63. Spring 63 is used to return impact plunger 65 of the dislodge solenoid. The impact of the plunger upon its return transmits a mechanical shock or vibration to mercury capillary tube 35, dislodging mercury drop 61.

As shown, dislodge solenoid 24 is contained within a housing 66. Housing 66 is coupled to the dispense valve through backup plate 60, via screws 70.

Figure 5:
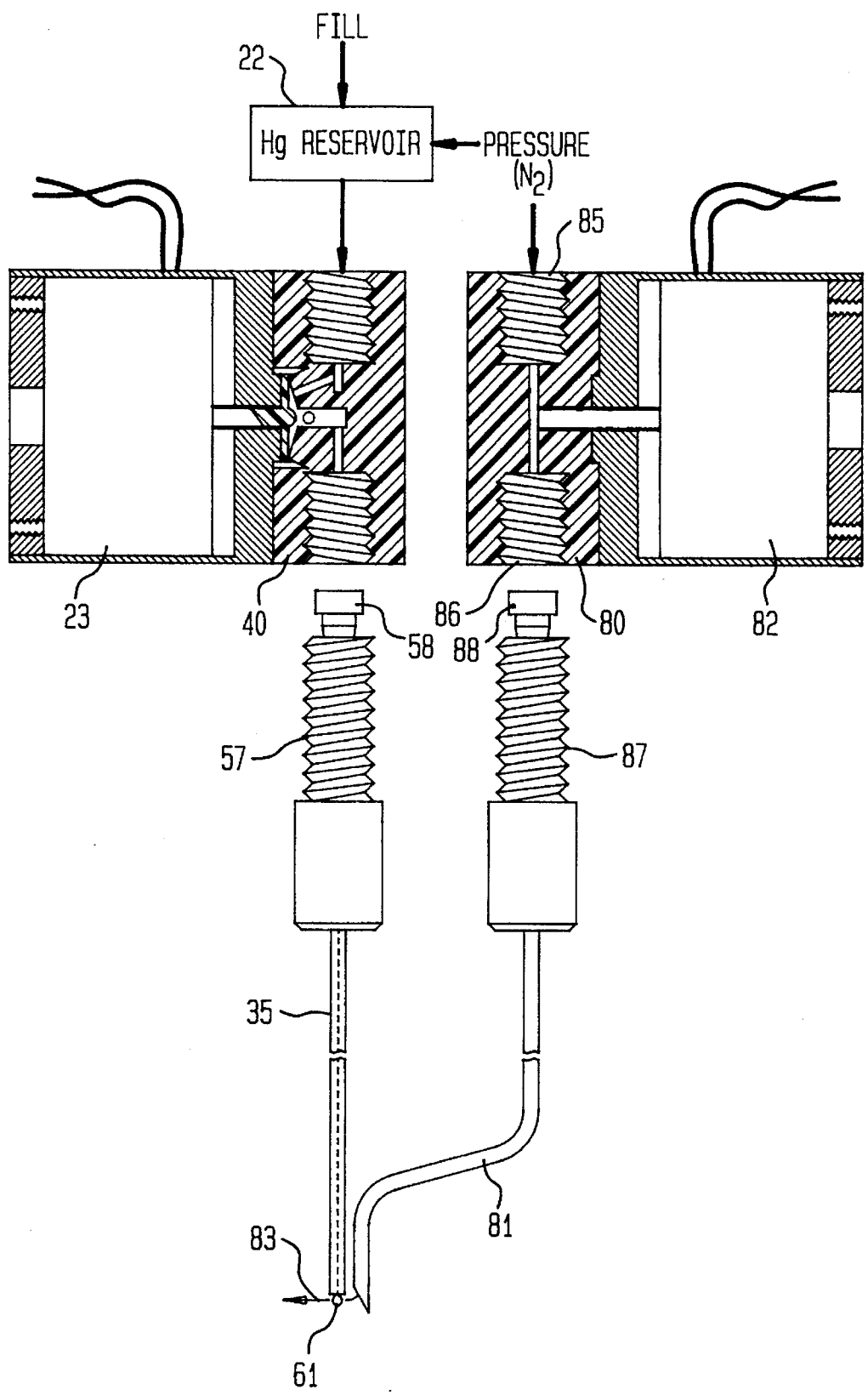
FIG. 5 is a partially cross-sectional exploded illustration of a dispense solenoid and the dislodge solenoid assembly for remote operation of specialized capillaries.

FIG. 5 is a partially cross-sectional exploded illustration of a further embodiment of the invention wherein the mercury drop is dislodged in response to the application of a stream of pressurized gas. In this specific illustrative embodiment of the invention, dispense valve 40, dispense solenoid 23, and mercury capillary tube 35 are as previously described. There is provided, however, a gas valve 80 which is operated in response to a gas dispense solenoid 82. The gas valve and the gas dispense solenoid are used in combination to produce a pulse of gas out of the end of gas capillary 81, which is directed in the direction of arrow 83, across mercury drop 61. In this embodiment, gas capillary 81 is cut at a 45° angle so that the exiting gas pulse will be directed in the direction of arrow 83. Of course, in other embodiments, the gas capillary may be axially directed toward the mercury drop.

The pressurized gas for operation of the gas-induced dislodgement of the mercury drop may be obtained, in certain embodiments, from a local source of pressurized nitrogen ($N_2$). The pressurized gas is delivered to a gas inlet 85 of gas valve 80, and in response to the actuation of gas dispense solenoid 82, is propagated to gas outlet 86 of the gas valve. Gas capillary 81 is coupled to the gas valve via a securing nut 87 and an associated sealing ferrule 88.

Figure 6:
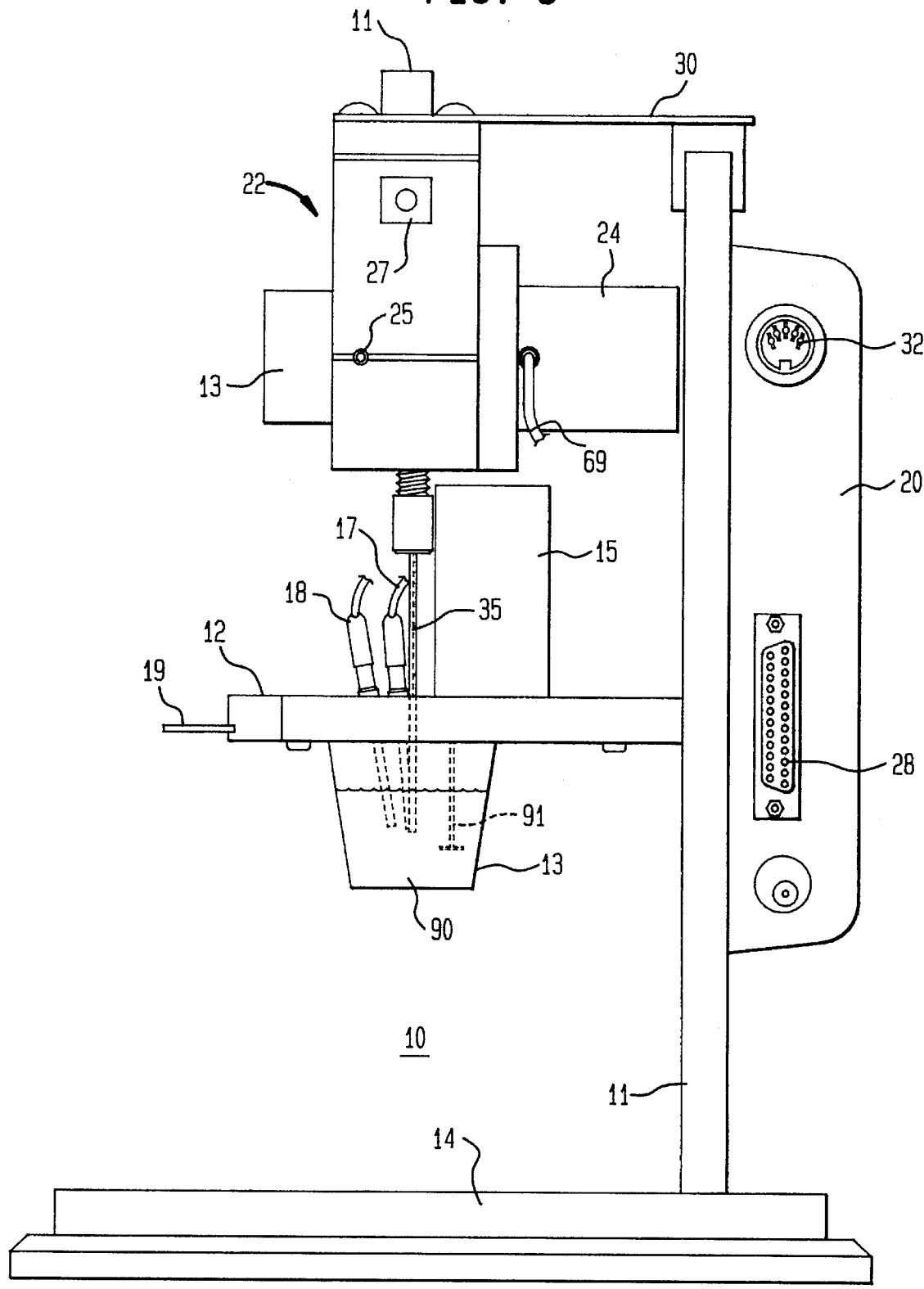
FIG. 6 is a side plan view of the mercury electrode assembly.

FIG. 6 is a side plan view of the mercury electrode system 10, which is also shown in FIG. 1. Elements of structure in FIG. 6 which bear correspondence to elements in FIG. 1 are similarly designated. FIG. 6 shows electrochemical cell 13 in phantom representation so that sample solution 90 can be seen. The sample solution is stirred by stirrer 15 which is shown to have an agitator 91 extending into the sample solution. This figure additionally shows reference electrode 18, counter electrode 17, and mercury capillary tube 35 in communication with the sample solution. The counter electrode usually is formed of platinum.

Figure 7:
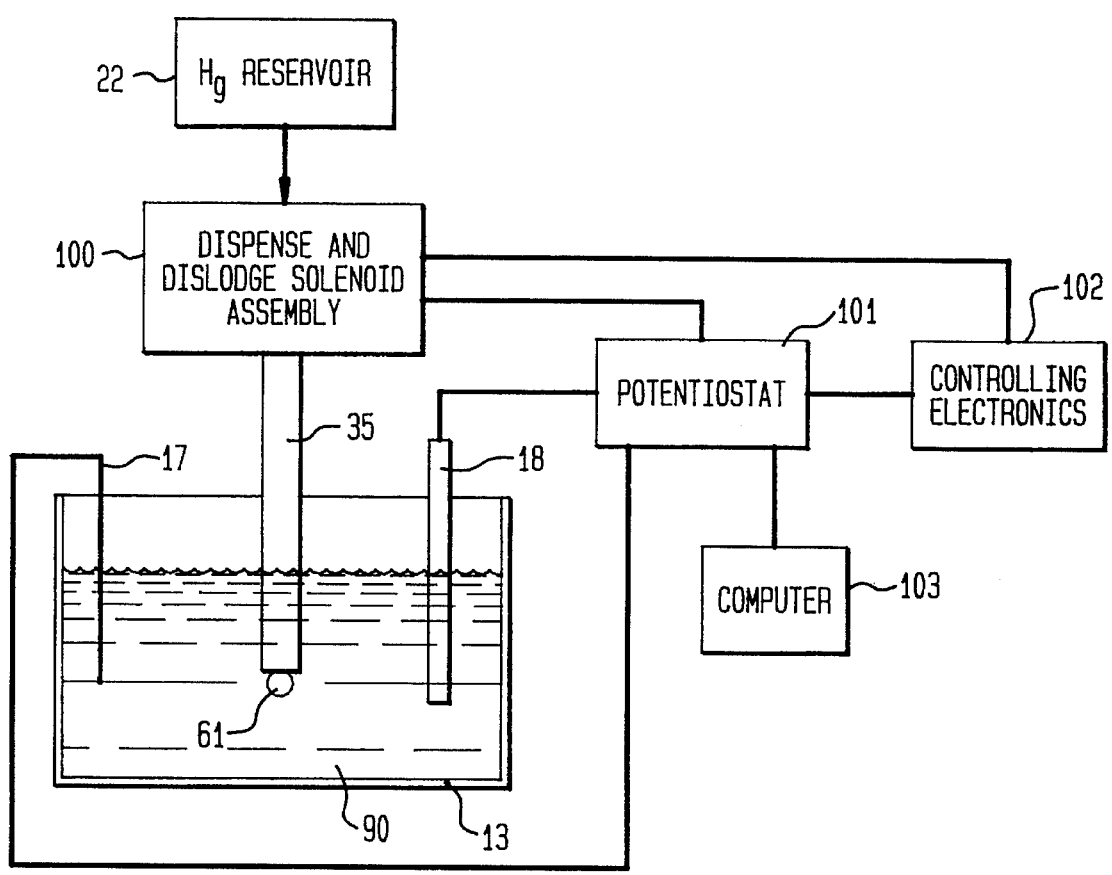
FIG. 7 is a block diagram which is useful in describing the operation of a hanging mercury drop system.

FIG. 7 is a block diagram which is useful in describing the operation of a hanging mercury drop system. Elements of structure in FIG. 7 which bear correspondence to elements in FIG. 1 through 6 are similarly designated. In this figure, dispense solenoid 23 and dislodge solenoid 24 are schematically represented by block 100. In this specific illustrative embodiment of the invention, these elements of structure operate as previously described in connection with FIG. 1, and control the dispensing of mercury from mercury reservoir 22, as previously described. There is additionally shown in this figure; counter electrode 17 (formed of platinum); reference electrode 18; mercury capillary tube 35 with mercury drop 61 hanging from the end thereof; a potentiostat 101; controlling electronics 102; and a data output device in the form of a computer 103.

The basic mode of operation is that the mercury material itself, in the form of hanging drop 61, becomes the electrode to be used in the study of sample solution 90. Since the mercury drop electrode can become unclean during the course of an electrochemical experiment, a new drop of mercury can be deposited on the end of mercury capillary tube 35 immersed in the solution under study. Thus, for each electrochemical experiment a new drop of mercury can be deposited on the end of the capillary.

Mercury contained in mercury reservoir 22 is, as described hereinabove with respect to FIGS. 2–5, conducted though the valve system. The diaphragm-like valve used in the system of the present invention allows for the flow of mercury to be interrupted when a drop is formed on the end of a capillary, and serves to isolate the mercury in mercury capillary tube 35 from the large mass of mercury in the reservoir. The valve, which can be operated under computer control, is opened so that the mercury can flow from the reservoir, through the valve, and down through the capillary, at which time a drop of mercury having predetermined and reproducible dimensions is formed at the end of mercury capillary tube 35. The closure of the dispense valve holds the hanging drop of mercury static. It is known to persons of skill in the art that the preferred mercury drop should have a substantially spherical configuration to achieve good electrical characteristics, and should extend beyond its capillary bore to avoid contamination of the capillary tip. However, the ill-effects of contamination of the capillary tip are ameliorated in the system of the present invention where mercury capillary tube 35 can function as a microelectrode, and can easily be removed for replacement or cleaning.

Potentiostat 101 is electrically coupled to sample solution 90 via mercury drop 61, counter electrode 17, and reference electrode 18. A scan of potential is made between the working electrode (i.e., the mercury drop of mercury capillary tube 35) and reference electrode 18. The resultant current through the sample solution is measured between the working electrode and the counter electrode. Once this analysis is performed a new drop can be manually dispensed, or dispensed remotely or automatically using computer control.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A mercury drop electrode arrangement comprising:

a reservoir for providing a source of liquid mercury;

a mercury capillary tube having an inlet, an outlet, and a mercury channel interconnecting the inlet and outlet, for receiving at said inlet liquid mercury from said reservoir and providing at said outlet a mercury drop;

a dispense valve coupled at a reservoir inlet thereof to said reservoir and at a reservoir outlet thereof to said mercury capillary tube for controlling a flow of the liquid mercury from said reservoir and said mercury capillary tube via a flow path therein; and actuator means coupled to said dispense valve, said actuator means having first and second states, whereby when said actuator means is in said first state, said dispense valve is in a closed state the flow of the liquid mercury from said reservoir and said mercury capillary tube is discontinued and the liquid mercury in said reservoir is isolated electrically from the mercury drop at said outlet of said mercury capillary tube, and whereby when said actuator means is in said second state, said dispense valve is in an open state and the flow of the liquid mercury from said reservoir and said mercury capillary tube is facilitated.

2. The mercury drop electrode arrangement of claim 1, wherein there is further provided diaphragm means in said dispense valve and coupled to said actuator means for being interposed in the flow path of said dispense valve and interrupting the flow of the liquid mercury from said reservoir and said mercury capillary tube when said actuator means is in said first state.

3. The mercury drop electrode arrangement of claim 2, wherein said diaphragm means displaces a portion of the mercury in said flow path, whereby the mercury in said reservoir is isolated electrically from the mercury drop at said outlet of said mercury capillary tube.

4. The mercury drop electrode arrangement of claim 1, wherein there is further provided:

a contact region in the flow path of said dispense valve; and contact means having a mercury contact portion for communicating with the mercury in said contact region in the flow path of said dispense valve, and a terminal portion extending outward of said dispense valve for providing an electrical output signal responsive to the mercury in said contact region.

5. The mercury drop electrode arrangement of claim 1, wherein said mercury capillary tube is formed of fused silica.

6. The mercury drop electrode arrangement of claim 1, wherein said mercury capillary tube is formed of polyetheretherketone.

7. The mercury drop electrode arrangement of claim 1, wherein there is further provided pressure port means coupled to said reservoir for delivering a pressurized gas to said liquid mercury.

8. The mercury drop electrode arrangement of claim 1, wherein there is further provided mercury dislodge means for removing the mercury drop at said outlet of said mercury capillary tube.

9. The mercury drop electrode arrangement of claim 8, wherein said mercury dislodge means comprises:

dislodge solenoid means for producing a mechanical shock upon being actuated electrically;

coupling means for transmitting the mechanical shock from said dislodge solenoid means to said dispense valve.

10. The mercury drop electrode arrangement of claim 9, wherein said dislodge solenoid means comprises:

a plunger for moving in a set direction upon applying an electrical actuation energy to said dislodge solenoid; and energy storage means for storing energy when said plunger is urged in said set direction and releasing said stored energy when said electrical actuation energy to said dislodge solenoid is discontinued.

11. The mercury drop electrode arrangement of claim 8, wherein said mercury dislodge means comprises:

gas dispense valve means having a gas inlet and a gas outlet for controlling the flow of a pressurized gas therebetween;

gas capillary means having a gas capillary inlet coupled to said gas outlet, and a gas capillary outlet arranged in the vicinity of said outlet of said mercury capillary tube, wherein a pressurized gas flowing through said gas dispense valve and said gas capillary means will dislodge and remove said mercury drop at said outlet of said mercury capillary tube.

12. A mercury drop electrode arrangement comprising:

a reservoir for providing a source of liquid mercury;

a mercury capillary tube having an inlet, an outlet, and a mercury channel interconnecting the inlet and outlet, for receiving at said inlet liquid mercury from said reservoir and providing at said outlet a mercury drop;

a dispense valve coupled at a reservoir inlet thereof to said reservoir and at a reservoir outlet thereof to said mercury capillary tube for controlling a flow of the liquid mercury from said reservoir and said mercury capillary tube via a flow path therein, said dispense valve further having:

a contact region interposed between said reservoir inlet and said reservoir outlet;

a reservoir mercury path for channeling mercury from said reservoir inlet to said contact region, said reservoir mercury path having a reservoir mercury path outlet arranged distal from said reservoir inlet;

an outlet mercury path for channeling mercury from said contact region to said reservoir outlet; and diaphragm means for closing said reservoir mercury path outlet; and actuator means coupled to said diaphragm means for urging said diaphragm means selectably between closed and open positions with respect to said reservoir mercury path outlet.

13. The mercury drop electrode arrangement of claim 12, wherein said diaphragm means is electrically non-conductive, and electrically isolates the mercury in said reservoir from said mercury capillary tube.

14. The mercury drop electrode arrangement of claim 12, wherein there is further provided contact means arranged to communicate electrically with said contact region of said dispense valve.

15. The mercury drop electrode arrangement of claim 12, wherein said reservoir comprises a squeezable container for urging mercury through said dispense valve and said mercury capillary tube.

16. The mercury drop electrode arrangement of claim 12, wherein there is further provided mercury dislodge means comprising:

dislodge solenoid means for producing an electromagnetic force upon being actuated electrically;

a plunger for moving in a set direction in response to said electromagnetic force;

energy storage means for storing energy when said plunger is urged in said set direction and releasing said stored energy when said electrical actuation energy to said dislodge solenoid is discontinued; and backup plate coupling means for coupling said dislodge solenoid to said dispense valve and transmitting a mechanical shock from said dislodge solenoid means to said dispense valve.

17. The mercury drop electrode arrangement of claim 12, wherein said mercury dislodge means comprises:

gas dispense valve means having a gas inlet and a gas outlet for controlling the flow of a pressurized gas therebetween;

gas capillary means having a gas capillary inlet coupled to said gas outlet, and a gas capillary outlet arranged in the vicinity of said outlet of said mercury capillary tube, wherein a pressurized gas flowing through said gas dispense valve and said gas capillary means will dislodge and remove said mercury drop at said outlet of said mercury capillary tube.

18. A method of acquiring an electrical signal from a hanging drop of mercury, the method comprising the steps of:

urging mercury stored in a reservoir of mercury to flow through a valve in an open state and to flow through a mercury capillary tube to form the drop of mercury at a distal end of the mercury capillary tube;

closing the valve to discontinue the flow of mercury through the mercury capillary tube;

electrically isolating the mercury stored in the reservoir from the mercury in the mercury capillary tube, and measuring electrical potential of the mercury stored in the reservoir wherein the potential is the electrical signal.

19. The method of claim 18 wherein said step of measuring further comprises step of communicating electrically with the drop of mercury, via the mercury in the mercury capillary tube, and via a contact extending through a wall of the valve.

20. The method of claim 18 wherein there are provided the further steps of:

dislodging the drop of mercury from the distal end of the mercury capillary tube;

opening the valve to resume the flow of mercury through the mercury capillary tube; and repeating said steps of urging mercury, closing the valve, electrically isolating, and measuring the electrical signal.

* * * * *